United States Patent [19]

Fuchs et al.

[11] 3,960,916

[45] June 1, 1976

[54] MANUFACTURE OF ORGANIC ISOCYANATES

[75] Inventors: Werner Fuchs, Ludwigshafen; Rolf Platz, Mannheim; Volker Vogt, Ludwigshafen, all of Germany

[73] Assignee: BASF Aktiengesellschaft, Ludwigshafen (Rhine), Germany

[22] Filed: Jan. 24, 1975

[21] Appl. No.: 543,693

Foreign Application Priority Data

Feb. 1, 1974 Germany.................... 2404774

[52] U.S. Cl. ........................................ 260/453 PH
[51] Int. Cl.² ...................................... C07C 118/02
[58] Field of Search ............................ 260/453 PH

[56] References Cited
UNITED STATES PATENTS

| | | | |
|---|---|---|---|
| 2,326,501 | 8/1943 | Siefken et al. | 260/453 |
| 3,631,092 | 12/1971 | Kan et al. | 260/453 |

*Primary Examiner*—Lewis Gotts
*Assistant Examiner*—Dolph H. Torrence
*Attorney, Agent, or Firm*—Johnston, Keil, Thompson & Shurtleff

[57] ABSTRACT

Organic isocyanates are manufactured, in the absence of organic solvents, by reaction of primary organic amines with hydrogen chloride, to give amine hydrochlorides, subsequent phosgenation, and thermal decomposition of the carbamyl chlorides formed as intermediates.

8 Claims, No Drawings

MANUFACTURE OF ORGANIC ISOCYANATES

This application discloses and claims subject matter described in German Patent application No. 2404774, filed Feb. 1, 1974, which is incorporated herein by reference.

The present invention relates to a process for the manufacture of organic monoisocyanates, diisocyanates and/or polyisocyanates for primary organic amines and phosgene, wherein the manufacture of the amine hydrochlorides and their phosgenation are carried out in the absence of solvents.

In the conventional manufacture of organic monoisocyanates and polyisocyanates by phosgenation of primary amines or their hydrochlorides, the amine hydrochlorides are obtained by dissolving the amines in inert organic solvents and precipitating the salts with hydrogen chloride. It is a disadvantage of this process that amine hydrochlorides which do not contain the stoichiometric amount of chemically bonded hydrogen chloride are frequently obtained under the conditions under which the precipitation takes place. The reason is that the amine hydrochloride which is produced spontaneously on reaction of amine with hydrogen chloride and which is virtually insoluble in the inert solvents used always occludes some free amine and prevents the latter from reacting with the hydrogen chloride. During the subsequent phosgenation of the amine hydrochlorides at elevated temperatures, the free amines can form undesired by-products, for example urea. Furthermore, these methods of precipitation frequently give very coarsely crystalline modifications of the amine hydrochlorides, so that the phosgenation requires long reaction times and this in turn favors the formation of undesirable by-products, with simultaneous decrease in yield, at the relatively high temperatures used in the manufacture of the isocyanates.

Finally, such processes using solvents are also expensive because of the need to separate the solvents from the reaction mixtures and/or end products, and regenerate them, and the consequent losses of solvents. For example, the solvents must be absolutely free from phosgene — which is only achievable by an expensive purification process — if they are to be reused for the manufacture of the amine hydrochloride. Further, almost all solvents form at least small amounts of by-products under the phosgenation reaction conditions, and these by-products may interfere with the course of the reaction and make it more difficult to purify the isocyanates.

If the solvents are removed before the phosgenation reaction, expensive apparatus is required and significant amounts of solvent may be lost.

It is an object of the present invention to manufacture isocyanates from primary organic amines and phosgene by a process which does not suffer from the disadvantages described.

We have found that isocyanates are obtained in high yields from organic primary amines and phosgene by a process wherein the primary amines are mixed with at least one mole of hydrogen chloride per amino group in the absence of organic solvents and the reaction mixture is at the same time ground to an average particle size of from 1 to 100$\mu$, and the resulting suspension of amine hydrochloride in hydrogen chloride and optionally in phosgene is converted, in the presence of at least 2 moles of phosgene per equivalent of amine hydrochloride and in the absence of solvents, into the corresponding isocyanates, via the carbamyl chlorides produced as intermediates, at temperatures of from 100° to 180°C and pressures of from 40 to 55 bars.

Numerous cycloaliphatic, araliphatic and, preferably, aliphatic and aromatic compounds containing at least one primary amino group per molecule can be used for the manufacture of the isocyanates. The use of the industrially important primary diamines and polyamines is preferred. The following may be mentioned as individual examples: cycloaliphatic monoamines of 5 to 12 carbon atoms, preferably of 5 to 8 carbon atoms, in the cycloalkyl radical, such as cyclohexylamine and cyclooctylamine, and, preferentially, cycloaliphatic diamines of 6 to 13 carbon atoms, such as cyclohexyldiamine and 4,4'-, 4,2'- and 2,2'-diaminodicyclohexylmethane; ar-aliphatic monoamines of 1 to 12 carbon atoms, preferably of 1 to 8 carbon atoms, such as benzylamine, 2-aminoethylbenzene and $\beta$-aminomethylnaphthalene and, preferentially, araliphatic diamines of 8 to 14 carbon atoms, such as xylylenediamine; aliphatic monoamines of 1 to 12 carbon atoms, preferably of 1 to 6 carbon atoms, such as methylamine, ethylamine, butylamine, octylamine, decylamine and dodecylamine and, preferentially, aliphatic diamines of 2 to 6 carbon atoms, such as 1,2-diaminoethane, 1,4-diaminobutane and preferentially 1,6-diaminohexane; aromatic monoamines of 6 to 18 carbon atoms, such as aniline, toluidine and naphthylamine, and, preferentially, aromatic diamines of 6 to 15 carbon atoms, such as phenylenediamine, naphthylenediamine, fluorenediamine, diphenyldiamine, anthracenediamine and preferentially, 2,4- and 2,6-toluylenediamine and 4,4'-, 2,4'- and 2,2'-diaminodiphenylmethane, and aromatic polyamines, such as 2,4,6-triaminotoluene and polyphenyl-polymethylene-polyamines and, preferentially, mixtures and diaminodiphenylmethanes and polyphenyl-polymethylene-polyamines. Individual monoamines, diamines and polyamines, or mixtures thereof, may be converted into the amine hydrochlorides and subsequently be phosgenated. Instead of the free amines, mixtures of amines and amine hydrochlorides may be employed.

The isocyanates are manufactured in a two-stage reaction.

In the first reaction stage, the organic primary amines are converted into the amine hydrochlorides. Since the formation of the salt is carried out in the absence of organic solvents, it is convenient to use as excess of liquefied hydrogen chloride; the amounts of hydrogen chloride used are advantageously such that at least one mole, and preferably from 5 to 60 moles, of hydrogen chloride are present in the reaction mixture per (mole of) amino group of the organic amine, and/or that a suspension of amine hydrochloride in hydrogen chloride, which has a solids content of from 5 to 25% by weight, preferably of from 10 to 20% by weight, based on the total weight of the suspension, is formed. Under appropriate circumstances it is possible to produce suspensions which have a lower or higher solids content than the above range and which contain phosgene as a diluent in addition to hydrogen chloride.

The phosgenation of the amine hydrochlorides and the decomposition of the carbamyl chlorides is carried out in the second reaction stage, again in the absence of solvents. In this stage, at least two, and preferably from 3 to 8, moles of phosgene are usually employed per (mole of) amine hydrochloride group of the primary organic amine.

A simplified process for the manufacture of diisocyanates or polyisocyanates by phosgenation of the diamine and polyamine intermediates formed by condensation of formaldehyde and aniline using acid catalysts, which gives polyisocyanates particularly suitable for use as wood glues, comprises a. a first stage in which aniline and aqueous formaldehyde are condensed in the presence of hydrochloric acid and the reaction mixture is distilled, without having been neutralized, and water and/or unconverted aniline are separated off and recycled if appropriate, and b. a second stage in which the polyamine/polyamine hydrochloride mixture which is obtained in the first stage and has not been neutralized is converted into polyamine hydrochloride by the method according to the invention, in liquid hydrogen chloride as the suspending medium, and the hydrochloride is reacted with liquid phosgene to give the polyisocyanate.

All conventional industrial processes produce the polyisocyanates at greater cost than permits their economical use as adhesives for chipboard, where the quality standards are not particularly high.

A particularly important aspect of the first stage of the process is that neutralization of the hydrochloric acid used as the catalyst is dispensed with and the polyamines are not isolated as free bases, but are obtained in the form of a mixture of free base and amine hydrochloride.

Since, at temperatures below 120°C, the polyamines are more or less viscous liquids whilst the hydrochlorides are solid saltlike products, it is advantageous to choose the amount of hydrochloric acid used to be such that the polyamine/polyamine hydrochloride mixture formed melts below 120°C. If the mixture melts above 120°C it is possible that on prolonged exposure to these conditions the primary free amino groups react, in the presence of amine hydrochlorides, to give undesirable secondary products.

If the polyamine/polyamine hydrochloride mixtures are obtained in the form of melts, both the removal of water and excess aniline by distillation, and the subsequent phosgenation, are facilitated.

To obtain such fusible intermediate products, which preferably melt below 120°C, the molar ratio of aniline to hydrochloric acid should be from 15:1 to 160:1 in the first stage of the reaction.

The properties, and especially the viscosity, of the polyisocyanate end product are particularly affected by the molar ratio of aniline to formaldehyde. This ratio can be varied from 4.0:1 to 1.5:1, preferably from 1.8 to 1 to 2.5:1, depending on the desired properties of the product. The hydrochloric acid catalyst used in the first stage of the reaction can be an aqueous solution of a gas. In the latter case, it is advantageous to use some of the hydrogen chloride liberated during the phosgenation stage.

The reaction of aniline with formaldehyde in the presence of hydrochloric acid is initially preferably carried out at temperatures from 20° to 50°C. Preferably, this temperature is raised to from 80° to 150°C, preferably to from 100 to 120°C, as soon as the Schiff's bases ae formed, since the reaction does not go to completion below 80°C. The change from the lower to the higher reaction temperature range can be effected stepwise or continuously, and rapidly or slowly.

In detail, the isocyanates are manufactured as follows: in the first reaction stage, the primary organic amines and the hydrogen chloride are mixed at from $-110°C$ to $+50°C$, preferably at from $-30°C$ to $+40°C$, under normal pressure or superatmospheric pressure, preferably at from 10 to 60 bars, and especially at from 14 to 55 bars, and at the same time the reaction mixture is ground to an average particle size of from 1 to $100\mu$, preferably of from 1 to $50\mu$. The primary amine is preferably in the form of a liquid, of a melt or, if appropriate, of a powder, when introduced into the liquid hydrogen chloride. Since the salt is in the main formed in a heterogeneous phase at the surface of the particles, the primary organic amines and the hydrogen chloride must be mixed vigorously and the instantaneously produced reaction mixture of amine and amine hydrochloride must be finely ground, and suspended in the hydrogen chloride, as rapidly as possible. Only by this method is it possible to manufacture finely crystalline amine hydrochlorides in which the constituents are present in the stoichiometric molar ratios, and which do not contain any occluded free amines.

Depending on the reactivity of the amine used and on the reaction conditions chosen, it may be advantageous to produce the amine hydrochloride in liquid phosgene, containing at least the amount of hydrogen chloride stoichiometrically required to form the hydrochloride, as the diluent. Mixtures of hydrogen chloride and phosgene in molar ratios of about from 1:1.5 to 1:8, preferably of from 1:3 to 1:8, are particularly suitable for this purpose. Such phosgene/hydrogen chloride mixtures of the desired composition can easily be isolated from the reaction mixture of the second reaction stage, and be recycled.

The mixing and simultaneous grinding are carried out in devices conventionally employed to grind, or enlarge the surface area of, solids and to manufacture suspensions of solids. Examples which may be mentioned are the Supraton machines (Deutsche Supraton Dusseldorf, West Germany), Turrax equipment (Janke & Kunkel KG, Staufen, West Germany) or Tornados (Emmendinger Maschinenfabrik GmbH, Emmendingen, West Germany). Grinding equipment wherein the grinding is carried out at energy densities of more than 5 kW/cubic meter of grinding volume, preferably at from 10 to 1,000 kW/cubic meter of grinding volume, are very suitable and are used preferentially. The mixing and grinding process is continued until all the primary amino groups have been converted to the corresponding amine hydrochloride groups. After a certain reaction time, the average particle size remains constant. The residence times for this stage of the reaction depend greatly on the reactivity of the amine used and on the efficiency of the mixing and grinding device and can vary from one second to 3 hours. However, it is preferred that residence times of from one second to 30 minutes should suffice to give quantitative conversion of the amine to amine hydrochloride.

This reaction stage can be carried out continuously by using a mixing and grinding device in which the reaction mixture is recycled, for example a recycling grinding pump. At fairly high throughputs, it is preferred to connect several, for example from 2 to 16, and preferably from 2 to 8, mixing and grinding devices in series or, if appropriate, in parallel and to feed the amine/hydrogen chloride mixture to them individually or conjointly.

The amine-free suspension of amine hydrochloride and hydrogen chloride, thus obtained, is phosgenated in the second reaction stage and the carbamyl chloride formed is converted to the corresponding isocyanate.

For the second stage, sufficient liquid phosgene to provide at least two moles of phosgene per equivalent of amine hydrochloride in the reaction mixture is introduced into the amine hydrochloride/hydrogen chloride suspension. If a larger molar excess, for example a three-fold to five-fold molar quantity, of phosgene is used, it may be desirable to remove a proportion of the hydrogen chloride from the amine hydrochloride/hydrogen chloride suspension before adding the phosgene.

If, on the other hand, the amine hydrochlorides are produced from the amine and a hydrogen chloride/phosgene mixture which has been isolated from the second reaction stage, and been recycled, the suspension obtained is used for the next stage without addition of extra phosgene.

The reactions which take place in the second reaction stage, namely the reaction of amine hydrochloride with phosgene to give carbamyl chloride and the decomposition of the latter to isocyanate and hydrogen chloride, are also carried out in the absence of organic solvents, with advantage in a heated pressure vessel, at from 100° to 180°C, preferably at from 120° to 160°C. In order to have a liquid hydrogen chloride/phosgene phase, the decomposition of the reaction mixture is carried out at pressures of from 14 to 55 bars, preferably of from 21 to 41 bars.

The phosgenation of the amine hydrochloride and the decomposition of the carbamyl chloride can be carried out in conventional reaction vessels. Examples are pressure vessels equipped with columns and condensers, in which excess phosgene is condensed in a condenser and fed, as the reflux, to the reaction mixture, whilst the hydrogen chloride eliminated is discharged continuously through a condenser and is optionally recycled to the first reaction stage. The reaction is preferably carried out in a column with a reboiler and top condenser; the reaction mixture is fed continuously to the column and the hydrogen chloride formed is discharged at the top of the column and the phosgene/isocyanate mixture at the bottom of the column. The phosgene/isocyanate mixture obtained can be fractionated, and purified, by distillation.

The monoisocyanates manufactured in accordance with the process are valuable intermediates for the manufacture of dyes, plant protection agents, textile auxiliaries and paper auxiliaries. The diisocyanates and/or polyisocyanates are used to manufacture polyurethane plastics, for example rigid, semirigid and soft foams, elastomers, surface coatings, filaments, adhesives and films.

In the Examples, the parts are by weight.

EXAMPLE 1

70 g of a melt, heated to 90°C, of 2,4-toluylenediamine and 2,6-toluylenediamine in the weight ratio of 80:20 are run dropwise into 400 g of liquid hydrogen chloride whilst mixing and grinding the batch with a Turrax TV 45 (Janke & Kunkel KG, Staufen, Breisgau, West Germany) at −100°C. After a residence time of 30 minutes, the bulk of the hydrogen chloride is distilled off and 400 g of liquid phosgene are introduced into the amine hydrochloride/hydrogen chloride suspension. The reaction mixture is raised to 0°C, transferred into a 600 ml steel autoclave surmounted by a condenser, and heated to 150°C whilst keeping the pressure at from 30 to 35 bars by releasing some of the continuously eliminated hydrogen chloride at the top of the condenser used to condense the phosgene. When the evolution of hydrogen chloride has ceased, the autoclave pressure is released, whereupon the excess phosgene distils off. The residual phosgene dissolved in the toluylenediisocyanate formed is removed by passing a stream of nitrogen through the mixture at 100°C. A distillation under reduced pressure, using a simple descending condenser, gives 90.8 g (90.8% of theory) of 99.9% pure toluylenediisocyanate mixture.

EXAMPLE 2

70 g of a melt, heated to 90°C, of 2,4-toluylenediamine and 2,6-toluylenediamine in the weight ratio of 80:20 are added dropwise to a liquid mixture of 380 g of phosgene and 42 g of hydrogen chloride whilst mixing and grinding the batch with a Turrax TV 45 at −70°C. After a residence time of 30 minutes the suspension is transferred into a 600 ml steel autoclave and the reaction is completed analogously to Example 1. 89.9 g (89.9% of theory) of a 99.9% pure toluylenediisocyanate mixture are obtained.

COMPARATIVE EXAMPLE 70 g of a melt, heated to 90°C, of 2,4-toluylenediamine and 2,6-toluylenediamine in the weight ratio of 80:20 are added dropwise to 398 g of liquid phosgene whilst mixing and grinding the batch with a Turrax TV 45 at 0°C. After a residence time of 30 minutes, the suspension is transferred in a 600 ml steel autoclave and the reaction is completed analogously to Example 1. 82 g (82% of theory) of a pure toluylenediisocyanate mixture are obtained.

EXAMPLE 3

60 g of a molten polyphenyl-polymethylene-polyamine mixture are added dropwise to 400 g of liquid hydrogen chloride whilst mixing and grinding the batch with the Turrax TV 45 at −100°C. After a residence time of 30 minutes at from −90° to −100°C the bulk of the hydrogen chloride is distilled off and 400 g of liquid phosgene are introduced into the amine hydrochloride suspension. The reaction mixture, raised to 0°C, is transferred into a 600 ml steel autoclave surmounted by a condenser and is heated to 150°C whilst keeping the pressure at from 30 to 35 bars by releasing the continuously eliminated hydrogen chloride at the top of the condenser used to condense the phosgene. When the evolution of hydrogen chloride has ceased, the autoclave pressure is released and the excess phosgene is distilled, in the course of 3 hours at 160°C and 5 mm Hg, from the isocyanate mixture formed. 65 g of a polyphenylpolymethylene-polyisocyanate mixture of viscosity 154 cSt at 25°C and NCO-number 31.4 are obtained.

EXAMPLE 4

60 g of a molten polyphenyl-polymethylene-polyamine mixture are added dropwise to a liquid mixture of 400 g of phosgene and 45 g of hydrogen chloride whilst mixing and grinding the batch with a Turrax TV 45 at −65°C. After a residence time of 30 minutes, the suspension is transferred into a 600 ml steel autoclave and the reaction is completed analogously to Example 3. 64.5 g of a polyphenyl-polymethylene-polyisocyanate mixture of viscosity 181 cSt at 25°C and NCO-number 31.3 are obtained.

EXAMPLE 5

200 parts of a 30% strength aqueous solution of formaldehyde are added to a mixture of 391 parts of aniline and 20 parts of 36% strength hydrochloric acid in the course of 30 minutes, whilst stirring, under conditions which keep the temperature below 50°C. Water is then distilled from the reaction mixture under atmospheric pressure until the bottoms temperature has risen to 120°C, the aniline which has distilled as an azeotrope being returned to the reaction mixture. The reaction has terminated after the residence time of 2 hours at 120°C and is then freed from residual traces of water and from unconverted aniline in a film evaporator (working on the Sambay system) at 150°C and 5 mm Hg. 60 parts of the resulting polyamine/polyamine hydrochloride mixture, in the form of a melt at 100°C, are added to 400 parts of hydrogen chloride at −100°C, the reaction mixture being stirred by means of a Turrax TV 45 turbomixer in order to mix the suspension thoroughly and grind the solid formed. After 30 minutes' mixing, the bulk of the hydrogen chloride is distilled off and 400 parts of liquid phosgene are added. The reaction mixture is raised to 0°C and then transferred into a 600 ml autoclave surmounted by a condenser. The autoclave is heated to 150°C whilst keeping the pressure at from 33 to 35 atmospheres gauge by releasing hydrogen chloride at the top of the condenser used to condense the phosgene. When the evolution of hydrogen chloride has ceased, the autoclave pressure is released, whereupon the excess phosgene distils off. The isocyanate mixture formed is freed from residual phosgene by 3 hours' treatment at 160°C and 5 mm Hg. The polyisocyanate mixture thus obtained (66 parts) has a viscosity of 166 cSt at 25°C and contains 31.5% of NCO groups.

EXAMPLE 6

100 parts of 1M aqueous hydrochloric acid are added to 335 parts of aniline, to give an amine/amine hydrochloride mixture. 200 parts of aqueous 30% strength formaldehyde solution are introduced into the mixture at a rate at which the reaction temperature remains below 40°C. When all the solution has been added, the reaction mixture is heated to 95°C and is kept at this temperature for 2 hours to complete the reaction. The bulk of the water is then distilled off azeotropically with aniline at atmospheric pressure in the course of one hour, after which residual water and aniline are removed in a film evaporator at 150°C/1 mm Hg, using an average residence time of 3 minutes. The resulting mixture of polyamines and polyamine hydrochloride, which is crystalline below 120°C, is cooled to room temperature and then ground in a ball mill; 60 parts of the product are introduced into 400 parts of liquid anhydrous hydrochloric acid using a powder feed screw. The suspension is ground and mixed for 30 minutes at −90°C with a Turrax TV 45 high intensity mixer. The temperature is than raised to 0°C and at the same time the hydrogen chloride which distils off is replaced by 400 parts by volume of phosgene. The reaction mixture is converted to the polyisocyanate in the autoclave described in Example 1, under the conditions stated in the same Example. The excess phosgene is distilled off and the last traces of phosgene are removed under reduced pressure at 160°C.

The polyisocyanate mixture obtained (66 parts) has a viscosity of 158 cSt at 25°C and contains 31.3% of NCO groups.

EXAMPLE 7

200 parts of 30% strength formaldehyde are introduced into an aniline/aniline hydrochloride mixture, obtained from 353 parts of aniline and 20 parts of 36% strength hydrochloric acid, at a rate at which the reaction temperature remains below 50°C. After all the formaldehyde has been added, the reaction mixture is heated to 120°C, in the course of which water distils off azeotropically with aniline. The aniline is returned to the reaction mixture and the reaction is completed in the course of 4 hours. A mixture of polyamine bases and polyamine hydrochloride is obtained after distillation in an evaporator at 150°C and 5 mm Hg to remove water and aniline; 60 parts of the molten mixture, at 120°C, are introduced into 400 parts of liquid hydrogen chloride. The solid in the resulting suspension is ground for 45 minutes at −90°C, the hydrogen chloride is then replaced by 400 parts of phosgene and the reaction mixture is raised to 0°C and transferred into the autoclave with reflux condenser, referred to earlier. The autoclave is heated to 150°C and the pressure is kept at 35 atmospheres gauge by releasing the HCl formed. When the evolution of HCl has ceased, the excess phosgene is distilled off and residual phosgene is removed at 160°C and 5 mm Hg. This gives a polyisocyanate mixture (65 parts) of viscosity 241 cSt at 25°C and NCO number 30.6.

EXAMPLE 8

200 parts of 30% strength aqueous formaldehyde are added to a mixture of 410 parts of aniline and 20 parts of 36% strength hydrochloric acid whilst thoroughly stirring the mixture and keeping the temperature below 50°C. The reaction is completed by heating the mixture to 120°C whilst distilling off water together with a little aniline. The aniline is returned to the mixture. The reaction is complete after 60 minutes at 120°C and the reaction mixture is then freed from residual water and aniline in a film-evaporator at 150°C and 5 mm Hg.

60 parts of the resulting polyamine/polyamine hydrochloride mixture, as a melt at 100°C, are introduced into 300 parts of liquid hydrogen chloride whilst thoroughly grinding the batch. After a residence time of 30 minutes at −90°C, the hydrogen chloride is replaced by 400 parts of phosgene and at the same time the suspension is raised to 0°C. The reaction mixture is transferred into the autoclave described in Example 1 and reacted, as described in the same Example, at 150°C and 35 atmospheres gauge, to give 66 parts of polyisocyanate. The phosgene-free polyisocyanate obtained has an NCO content of 31.7% and a viscosity of 94 cSt at 25°C.

We claim:
1. A method of preparing organic isocyanates which comprises:
   a. mixing a primary amine with at least one mole of hydrogen chloride per amino group of said primary amine in the absence of an organic solvent and simultaneosly grinding the reaction mixture to an average particle size of from about 1 to about 100μ and
   b. reacting the resulting suspension of amine hydrochloride in hydrogen chloride with at least 2 moles of phosgene per amine hydrochloride group in the absence of an organic solvent at a temperature of from about 100° to about 180°C and at a pressure of from about 14 to about 55 bar to form the corresponding isocyanate.

2. A process for the manufacture of organic isocyanates, as set forth in claim 1, wherein organic aliphatic, cycloaliphatic and aromatic diamines and/or polyamines are used as primary amines.

3. A process for the manufacture of organic isocyanates as set forth in claim 2, wherein 2,4-toluylenediamine, 2,6-toluylenediamine, mixtures of 2,4-toluylenediamine and 2,6-toluylenediamine, 4,4'-, 2,4'- and 2,2'-diaminodiphenylmethane, mixtures of 4,4'-, 2,4'- and 2,2'-diaminodiphenylmethanes, 2,4,6-triaminotoluene, mixtures of polyphenyl-polymethylene-polyamines and mixtures of diaminodiphenylmethanes and polyphenyl-polymethylene-polyamines are used as primary aromatic diamines and/or polyamines.

4. A process for the manufacture of organic isocyanates as set forth in claim 1, wherein from 5 to 25 moles of hydrogen chloride are used per amino group of the primary amine.

5. A process for the manufacture of organic isocyanates as set forth in claim 1, wherein from 3 to 8 moles of phosgene are used per amino group of the primary amine hydrochloride.

6. A process for the manufacture of organic isocyanates as set forth in claim 1, wherein the amine hydrochloride is formed in the presence of phosgene.

7. The method of preparing organic isocyanates as set forth in claim 6 which comprises:
 a. mixing a primary amine with at least one mole hydrogen chloride per amino group of said primary amine in the presence of at least 2 moles of phosgene per amino group of said primary amine in the absence of an organic solvent and simultaneously grinding the reaction mixture to an average particle size from about 1 to 100$\mu$ and
 b. heating the resulting suspension of amine hydrochloride and carbamyl chloride in a mixture of hydrogen chloride and phosgene in the absence of an organic solvent at a temperature of from about 100° to about 180°C and at a pressure of from about 14 to about 55 bar to form the corresponding isocyanate.

8. A process for the manufacture of organic isocyanates as set forth in claim 1, wherein the reaction mixture is ground at energy densities of about 10 to about 1,000 kW/cubic meter of grinding volume.

* * * * *